United States Patent
Harper

(10) Patent No.: US 12,226,089 B2
(45) Date of Patent: *Feb. 18, 2025

(54) SURGICAL TISSUE RETRACTOR HOLDING FRAME

(71) Applicant: Encore Medical, LP, Austin, TX (US)

(72) Inventor: Keith J Harper, Hixson, TN (US)

(73) Assignee: Encore Medical, LP, Austin, TX (US)

( * ) Notice: Subject to any disclaimer, the term of this patent is extended or adjusted under 35 U.S.C. 154(b) by 280 days.

This patent is subject to a terminal disclaimer.

(21) Appl. No.: 17/871,062

(22) Filed: Jul. 22, 2022

(65) Prior Publication Data
US 2023/0000479 A1    Jan. 5, 2023

Related U.S. Application Data

(63) Continuation of application No. 17/189,549, filed on Mar. 2, 2021, now Pat. No. 11,395,646.
(Continued)

(51) Int. Cl.
*A61B 17/02* (2006.01)
*A61B 17/00* (2006.01)
*A61B 90/50* (2016.01)

(52) U.S. Cl.
CPC ....... *A61B 17/0218* (2013.01); *A61B 2017/00477* (2013.01); *A61B 2017/00526* (2013.01); *A61B 90/50* (2016.02)

(58) Field of Classification Search
CPC . A61B 17/0206; A61B 17/0218; A61B 90/50; A61B 2017/00477; A61B 2017/00526
(Continued)

(56) References Cited

U.S. PATENT DOCUMENTS

| | | | |
|---|---|---|---|
| 3,509,873 A | 5/1970 | Karlin et al. | |
| 4,949,707 A | 8/1990 | LeVahn et al. | |

(Continued)

FOREIGN PATENT DOCUMENTS

| | | |
|---|---|---|
| JP | 2005532890 A | 11/2005 |
| JP | 2007289780 A | 11/2007 |
| WO | 2008055324 A2 | 5/2008 |

OTHER PUBLICATIONS

International Preliminary Report on Patentability dated Sep. 15, 2022 for PCT/US2021/020400.
(Continued)

*Primary Examiner* — Eduardo C Robert
*Assistant Examiner* — David C Comstock
(74) *Attorney, Agent, or Firm* — Veros Legal Solutions, LLP

(57) ABSTRACT

Retractor holding frames and related methods are provided. The frame includes a support body including a first bore extending transversely from a first side of the support body to a second side of the support body opposite the first side, and a second bore extending transversely from the second side to the first side. The frame includes a left support frame arm including a first annular hub configured to be disposed within the first bore and a first plurality of posts disposed along an outer edge of the left support frame arm configured to retain a first retractor in a first orientation. The frame includes a right support frame arm including a second annular hub configured to be disposed within the second bore and a second plurality of posts disposed along an outer edge of the right support frame arm configured to retain a second retractor in a second orientation.

18 Claims, 7 Drawing Sheets

Related U.S. Application Data

(60) Provisional application No. 62/984,363, filed on Mar. 3, 2020.

(58) Field of Classification Search
USPC .................. 600/210, 219, 224, 228, 231
See application file for complete search history.

(56) References Cited

U.S. PATENT DOCUMENTS

| | | | |
|---|---|---|---|
| 5,897,087 | A | 4/1999 | Farley |
| 6,659,945 | B2 | 12/2003 | Ball et al. |
| 6,663,563 | B1 * | 12/2003 | Sharratt ............ A61B 1/00149 |
| | | | 600/227 |
| 9,161,745 | B2 | 10/2015 | Dodson |
| 10,772,704 | B2 | 9/2020 | Garcia et al. |
| 11,395,646 | B2 * | 7/2022 | Harper .................. A61B 90/57 |
| 2004/0002633 | A1 | 1/2004 | Phillips et al. |
| 2005/0065410 | A1 | 3/2005 | Bjork et al. |
| 2005/0215865 | A1 | 9/2005 | LeVahn et al. |
| 2007/0213597 | A1 | 9/2007 | Wooster |
| 2013/0082157 | A1 | 4/2013 | Agbodoe et al. |
| 2013/0204091 | A1 | 8/2013 | Menendez et al. |
| 2018/0110505 | A1 * | 4/2018 | Farley .................. A61B 17/025 |
| 2021/0346006 | A1 | 11/2021 | Cestero et al. |

OTHER PUBLICATIONS

International Search Report dated Jun. 11, 2021 for PCT Application No. PCT/US2021/020400.

Written Opinion dated Jun. 11, 2021 for PCT Application No. PCT/US2021/020400.

\* cited by examiner

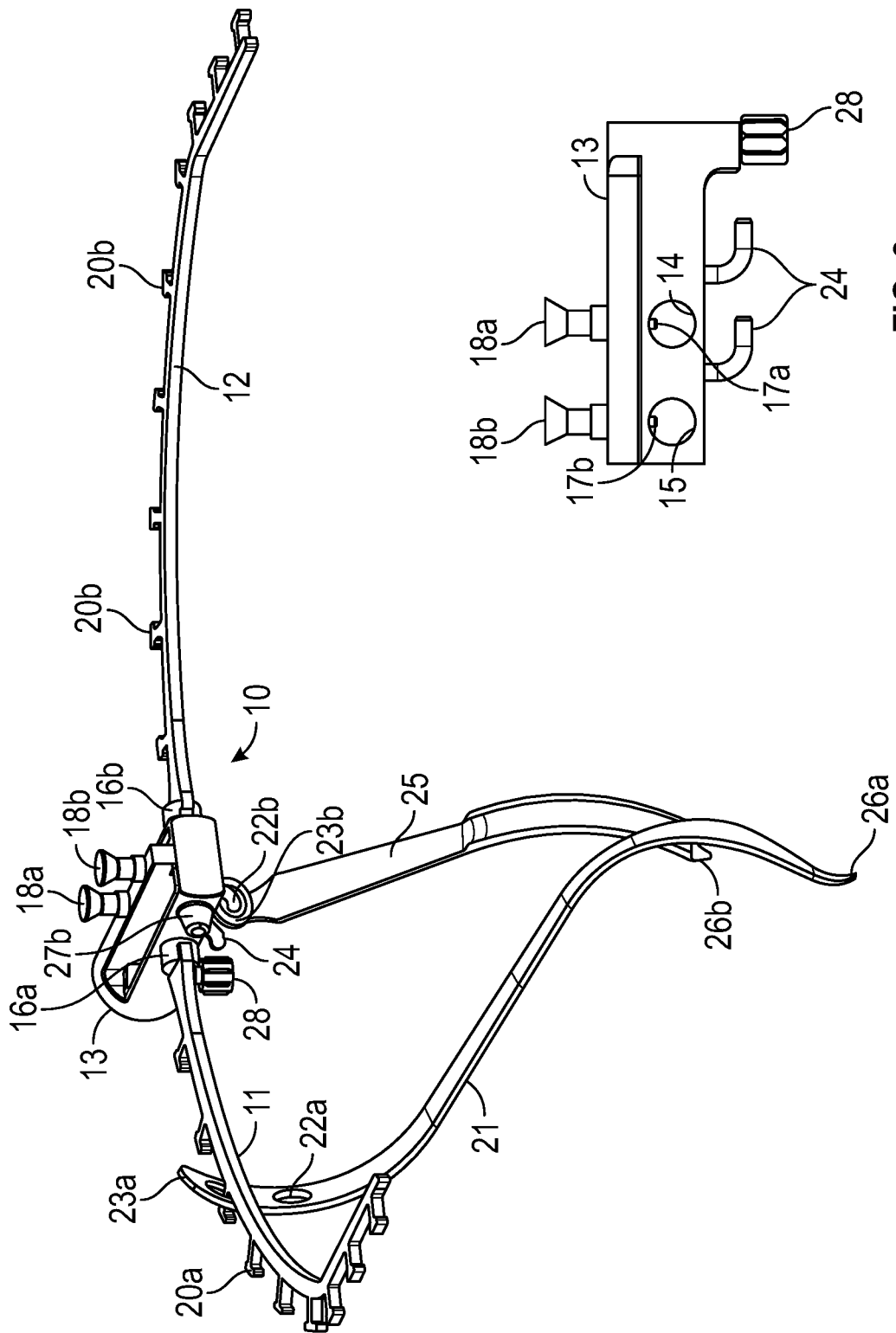

SURGICAL TISSUE RETRACTOR HOLDING FRAME

CROSS-REFERENCE TO RELATED APPLICATIONS

This application is a continuation of U.S. application Ser. No. 17/189,549, filed on Mar. 2, 2021, and will issue as U.S. Pat. No. 11,395,646 on Jul. 26, 2022, which claims priority to U.S. Provisional Application No. 62/984,363, filed on Mar. 3, 2020, the entire contents of which are hereby incorporated by reference.

FIELD OF THE INVENTION

The present invention relates generally to surgical retractors and more particularly, to a retractor frame holding assembly and related methods involving the same.

BACKGROUND

Open and mini-open surgical procedures require multiple instruments, e.g., for retracting and holding both instruments and the patient's tissue. There are many soft tissue surgical procedures, such as about the shoulder or hip, that require such an open or mini-open technique, as opposed to an arthroscopic technique. These open or mini-open procedures require expensive resources, including but not limited to additional staff surgeons and assistants to hold the various retraction and/or surgical instruments.

Unfortunately, such additional staff is costly and can provide inconsistent medical support (e.g., holding tissues in one or more retracted positions). Accordingly, there is a need for an effective and efficient retractor holding device to overcome the drawbacks associated with prior art retractor holders and techniques.

It should be noted that this Background is not intended to be an aid in determining the scope of the claimed subject matter nor be viewed as limiting the claimed subject matter to implementations that solve any or all of the disadvantages or problems presented above. The discussion of any technology, documents, or references in this Background section should not be interpreted as an admission that the material described is prior art to any of the subject matter claimed herein.

SUMMARY

In some embodiments, a retractor holding frame is provided. The frame includes a support body including a first bore extending transversely from a first side of the support body to a second side of the support body opposite the first side, and a second bore extending transversely from the second side to the first side. The frame includes a left support frame arm including a first annular hub configured to be disposed within the first bore and a first plurality of posts disposed along an outer edge of the left support frame arm configured to retain a first retractor in a first orientation. The frame includes a right support frame arm including a second annular hub configured to be disposed within the second bore and a second plurality of posts disposed along an outer edge of the right support frame arm configured to retain a second retractor in a second orientation.

In some other embodiments, a method of using a retractor holding frame is provided. The method includes inserting a first annular hub of a left support frame arm into a first bore of a support body. The first bore extends transversely through the support body from a first side of the support body to a second side of the support body opposite the first side. The method includes fixing the left support frame arm in a desired orientation with respect to the support body by disposing a first retaining pin of a first spring-biased locking mechanism of the support body down into the first bore such that the first retaining pin is received into one of a first annular series of detents disposed in the first annular hub of the left support frame arm. The method includes inserting a second annular hub of a right support frame arm into a second bore of the support body. The second bore extends transversely through the support body from the second side to the first side. The method includes fixing the right support frame arm in a desired orientation with respect to the support body by disposing a second retaining pin of a second spring-biased locking mechanism of the support body down into the second bore such that the second retaining pin is received into one of a second annular series of detents disposed in the second annular hub of the right support frame arm.

In some other embodiments, a method of manufacturing a retractor holding frame is provided. The method includes providing a support body having a first side and a second side opposite the first side. The method includes forming a first bore extending transversely through the support body from the first side to the second side. The method includes forming a second bore extending transversely through the support body from the second side to the first. The method includes providing a left support frame arm including a first annular hub configured to be disposed within the first bore of the support body, and a first plurality of posts disposed along an outer edge of the left support frame arm and configured to receive and retain at least a first retractor in a first desired orientation. The method includes providing a right support frame arm including a second annular hub configured to be disposed within the second bore of the support body, and a second plurality of posts disposed along an outer edge of the right support frame arm and configured to receive and retain at least a second retractor in a second desired orientation.

It is understood that various configurations of the subject technology will become apparent to those skilled in the art from the disclosure, wherein various configurations of the subject technology are shown and described by way of illustration. As will be realized, the subject technology is capable of other and different configurations and its several details are capable of modification in various other respects, all without departing from the scope of the subject technology. Accordingly, the summary, drawings and detailed description are to be regarded as illustrative in nature and not as restrictive.

BRIEF DESCRIPTION OF THE DRAWINGS

Various embodiments are discussed in detail in conjunction with the Figures described below, with an emphasis on highlighting the advantageous features. These embodiments are for illustrative purposes only and any scale that may be illustrated therein does not limit the scope of the technology disclosed. These drawings include the following figures, in which like numerals indicate like parts.

FIG. 1 is a left-side perspective view of a retractor holding frame, according to some embodiments;

FIG. 2 is an enlarged side elevation view of a support body of the retractor holding frame of FIG. 1, according to some embodiments;

DETAILED DESCRIPTION

Figure 3:
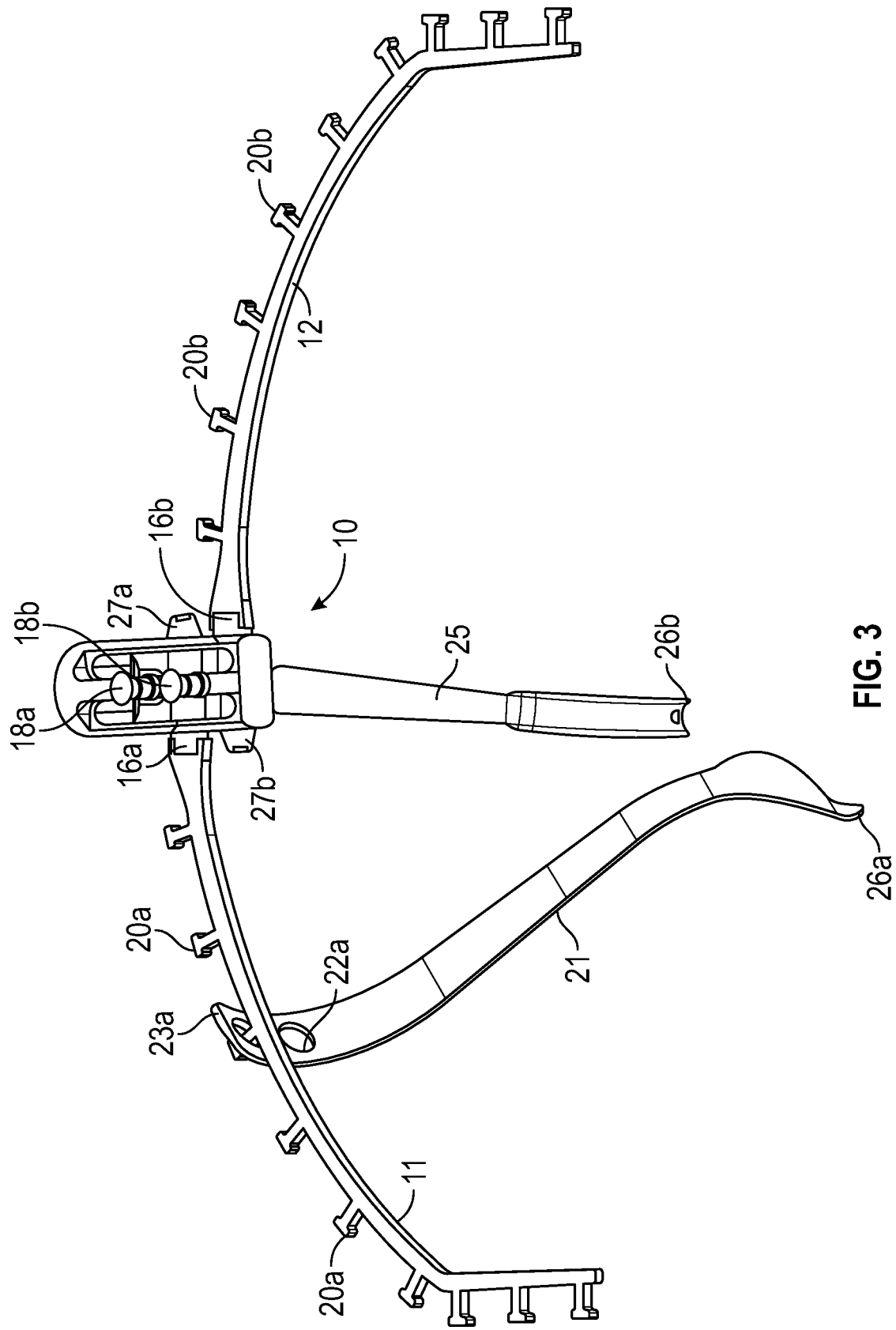
FIG. 3 is a center perspective view of the retractor holding frame of FIG. 1, according to some embodiments.

The following description and examples illustrate some exemplary implementations, embodiments, and arrangements of the disclosed invention in detail. Those of skill in the art will recognize that there are numerous variations and modifications of this invention that are encompassed by its scope. Accordingly, the description of a certain example embodiment should not be deemed to limit the scope of the present invention.

Implementations of the technology described herein are directed generally to a retractor holding frame assembly and related methods.

General Interpretive Principles for the Present Disclosure

Various aspects of the novel systems, apparatuses, and methods are described more fully hereinafter with reference to the accompanying drawings. The teachings disclosure may, however, be embodied in many different forms and should not be construed as limited to any specific structure or function presented throughout this disclosure. Rather, these aspects are provided so that this disclosure will be thorough and complete, and will fully convey the scope of the disclosure to those skilled in the art. Based on the teachings herein one skilled in the art should appreciate that the scope of the disclosure is intended to cover any aspect of the novel systems, apparatuses, and methods disclosed herein, whether implemented independently of or combined with any other aspect of the disclosure. For example, a system or an apparatus may be implemented, or a method may be practiced using any one or more of the aspects set forth herein. In addition, the scope of the disclosure is intended to cover such a system, apparatus or method which is practiced using other structure, functionality, or structure and functionality in addition to or other than the various aspects of the disclosure set forth herein. It should be understood that any aspect disclosed herein may be set forth in one or more elements of a claim. Although some benefits and advantages of the preferred aspects are mentioned, the scope of the disclosure is not intended to be limited to particular benefits, uses, or objectives. The detailed description and drawings are merely illustrative of the disclosure rather than limiting, the scope of the disclosure being defined by the appended claims and equivalents thereof.

With respect to the use of plural vs. singular terms herein, those having skill in the art can translate from the plural to the singular and/or from the singular to the plural as is appropriate to the context and/or application. The various singular/plural permutations may be expressly set forth herein for sake of clarity.

When describing an absolute value of a characteristic or property of a thing or act described herein, the terms "substantial," "substantially," "essentially," "approximately," and/or other terms or phrases of degree may be used without the specific recitation of a numerical range. When applied to a characteristic or property of a thing or act described herein, these terms refer to a range of the characteristic or property that is consistent with providing a desired function associated with that characteristic or property.

In those cases where a single numerical value is given for a characteristic or property, it is intended to be interpreted as at least covering deviations of that value within one significant digit of the numerical value given.

If a numerical value or range of numerical values is provided to define a characteristic or property of a thing or act described herein, whether or not the value or range is qualified with a term of degree, a specific method of measuring the characteristic or property may be defined herein as well. In the event no specific method of measuring the characteristic or property is defined herein, and there are different generally accepted methods of measurement for the characteristic or property, then the measurement method should be interpreted as the method of measurement that would most likely be adopted by one of ordinary skill in the art given the description and context of the characteristic or property. In the further event there is more than one method of measurement that is equally likely to be adopted by one of ordinary skill in the art to measure the characteristic or property, the value or range of values should be interpreted as being met regardless of which method of measurement is chosen.

It will be understood by those within the art that terms used herein, and especially in the appended claims (e.g., bodies of the appended claims) are intended as "open" terms unless specifically indicated otherwise (e.g., the term "including" should be interpreted as "including but not limited to," the term "having" should be interpreted as "having at least," the term "includes" should be interpreted as "includes but is not limited to," etc.).

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

In those instances where a convention analogous to "at least one of A, B, and C" is used, such a construction would include systems that have A alone, B alone, C alone, A and B together without C, A and C together without B, B and C together without A, as well as A, B, and C together. It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include A without B, B without A, as well as A and B together."

Various modifications to the implementations described in this disclosure can be readily apparent to those skilled in the art, and generic principles defined herein can be applied to other implementations without departing from the spirit or scope of this disclosure. Thus, the disclosure is not intended to be limited to the implementations shown herein but is to be accorded the widest scope consistent with the claims, the principles and the novel features disclosed herein. The word "exemplary" is used exclusively herein to mean "serving as an example, instance, or illustration." Any implementation described herein as "exemplary" is not necessarily to be construed as preferred or advantageous over other implementations.

Certain features that are described in this specification in the context of separate implementations also can be implemented in combination in a single implementation. Conversely, various features that are described in the context of a single implementation also can be implemented in multiple implementations separately or in any suitable sub-combination. Moreover, although features can be described above as acting in certain combinations and even initially claimed as such, one or more features from a claimed combination can in some cases be excised from the combination, and the claimed combination can be directed to a sub-combination or variation of a sub-combination.

Any methods disclosed herein comprise one or more steps or actions for achieving the described method. The method steps and/or actions may be interchanged with one another without departing from the scope of the claims. In other words, unless a specific order of steps or actions is specified, the order and/or use of specific steps and/or actions may be modified without departing from the scope of the claims.

Disclosure of Several Example Embodiments

Figure 4:
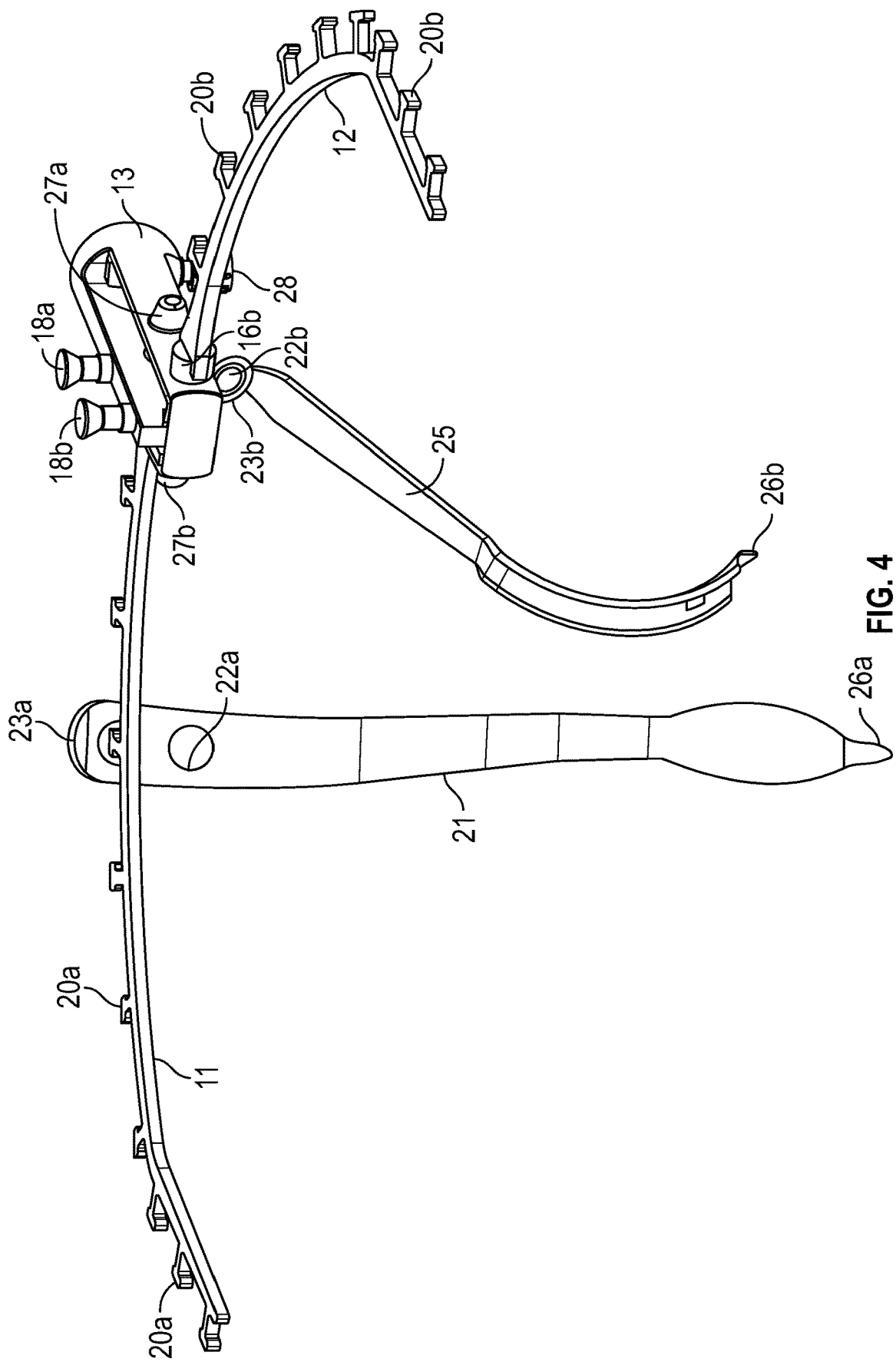
FIG. 4 is a right-side perspective view of the retractor holding frame of FIG. 1, according to some embodiments.

The present disclosure describes a retractor holding frame 10 attached or attachable to the side of a surgical table with an adjustable support arm. Several embodiments of retractor holding frame 10 will now be discussed in connection with FIGS. 1-8. FIG. 1 provides a left-side perspective view of retractor holding frame 10, while FIGS. 3 and 4 provide center and right-side perspective views of retractor holding frame 10, respectively.

Retractor holding frame 10 can include a left support frame arm 11 and a right support frame arm 12. Left and right support frame arms 11, 12 are each independently and adjustably supported by support body 13. Support body 13 is, in turn, adjustably supported from a surgical table by an adjustable support arm (not shown).

As best illustrated in the enlarged side elevation view of support body 13 of FIG. 2, support body 13 includes a first bore 14 extending transversely through support body 13 from a first side of support body 13 to a second side of support body 13 opposite the first side. Support body 13 also includes a second bore 15 extending transversely through support body 13 from the second side of support body 13 to the first side of support body 13. First bore 14 is configured to receive at least a portion of left support frame arm 11 at the first side of support body 13 and second bore 15 is configured to receive at least a portion of right support frame arm 12 at the second side of support body 13.

Figure 5:
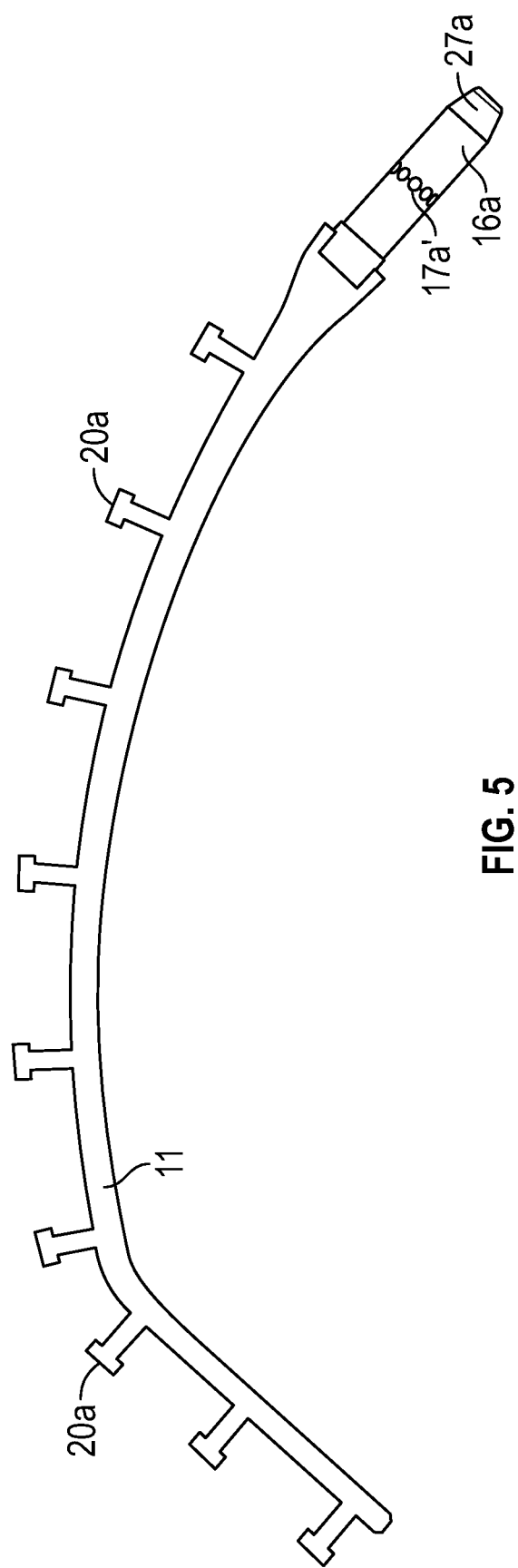
FIG. 5 is a top plan view of a left-side frame arm of the retractor holding frame of FIG. 1, according to some embodiments.
Figure 6:
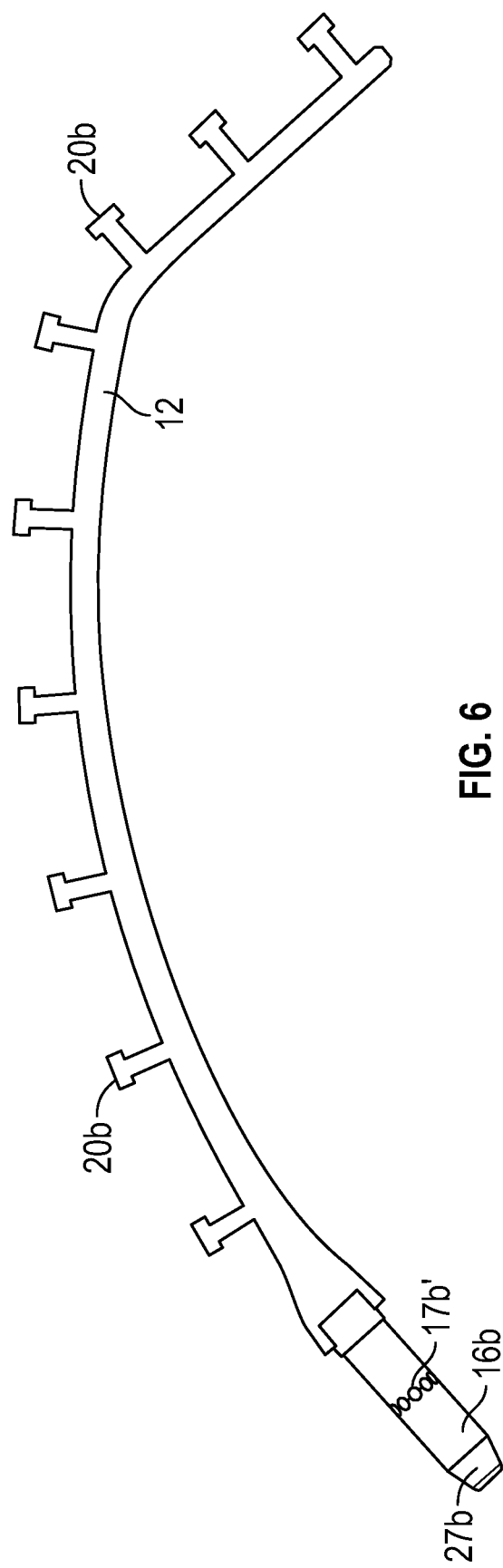
FIG. 6 is a top plan view of a right-side frame arm of the retractor holding frame of FIG. 1, according to some embodiments.

As best illustrated by the top plan view of left support frame arm 11 in FIG. 5, left support frame arm 11 is provided with an annular hub 16a configured to be disposed in first bore 14 in support body 13. Similarly, as best illustrated by the top plan view of right support frame arm 12 in FIG. 6, right support frame arm 12 is provided with an annular hub 16b configured to be disposed in second bore 15 in support body 13. In some embodiments, each of first and second bores 14, 15 and each of the respective first and second annular hubs 16a, 16b of left and right support frame arms 11, 12 have substantially circular cross-sections so as to allow respective annular hubs 16a, 16b of left and right support frame arms 11, 12 to fit and rotate within respective first and second bores 14, 15 of support body 13.

In some embodiments each of first and second annular hubs 16a, 16b have respective tapered distal ends 27a, 27b, which allow for easy alignment and insertion of respective first and second annular hubs 16a, 16b into respective first and second bores 14, 15.

In some embodiments, each of first and second annular hubs 16a, 16b further include a respective annular series of recesses or detents 17a', 17b' configured to selectively receive a respective retaining pin 17a, 17b of a respective spring-biased locking mechanism 18a, 18b disposed on a top surface of support body 13. As viewed in FIG. 2, respective retaining pins 17a, 17b are configured to extend down into respective first and second bores 14, 15, under force provided by respective spring-biased locking mechanisms 18a, 18b, and seat and/or index within a respective one of the respective annular series of recesses or detents 17a', 17b' of respective hubs 16a, 16b.

In operation, respective portions of spring-biased locking mechanisms 18a, 18b can be pulled upwardly to thereby retract respective retaining pins 17a, 17b sufficiently to allow respective annular hubs 16a, 16b of respective left and right support frame arms 11, 12 to be inserted into respective first and second bores 14, 15 and respective left and right support frame arms 11, 12 to be rotated to respective desired positions. Once left and right support frame arms 11, 12 are rotated to such respective desired positions, the respective portions of spring-biased locking mechanisms 18a, 18b can be released to thereby allow respective retaining pins 17a, 17b to extend back into respective first and second bores 14, 15 and seat and/or index within respective ones of the respective annular series of recesses or detents 17a', 17b' of respective hubs 16a, 16b. This permits selective rotating adjustment of frame arms 11 and 12 with respect to at least support body 13.

Support body 13 is further provided with a quick-connect connector 28 for coupling support body 13 to a positioning arm (not shown) which, in turn, adjustably supports retractor holding frame 10 from a surgical table. A number of conventional positioning arms are available on the market.

The present disclosure contemplates each of left and right support frame arms 11, 12 having any suitable shape. For example, in some embodiments, left and right support frame arms 11, 12 may have a substantially curved shape as illustrated in FIGS. 1 and 3-6. However, one or both of left and right support frame arms 11, 12 could also and/or alternatively have a substantially straight shape, or one or more portions may have a substantially curved shape, while one or more other portions may have a substantially curved shape to suit the particular application. Moreover, different sized and/or shaped left and right support frame arms 11, 12 may be readily substituted, inserted and/or removed from support body 13 as described above.

Left and right support frame arms 11, 12 each further include a respective plurality of retaining hooks or posts 20a, 20b disposed along their outside edges and configured to receive and retain one or more retractors 21 in position. For example, one or more retractors 21 may each be provided with a series of apertures 22a at a proximal end 23a and such apertures 22a are configured to receive one of hooks or posts 20a, 20b and thereby retain proximal ends 23a of retractors 21 on those respective hooks or posts 20a, 20b. Retractors 21 may have any suitable shape. For example, retractors 21 may have at least one curved portion. For example, as illustrated in FIGS. 1, 3 and 4, proximal 23a and distal 26a ends of retractor 21 can be substantially curved. In some embodiments, retractors 21 may have at least one substantially straight portion. For example, as illustrated in FIGS. 1, 3 and 4, a medial portion of retractor 21 can be substantially straight. In some embodiments, at least a portion of retractor 21 can be tapered. For example, as illustrated in FIGS. 1, 3 and 4, in some embodiments, retractor 21 can taper along its length of extension at least from its medial portion to distal end 26a. Such a tapered aspect may allow retractors 21 to more effectively focus retention force to a particular portion of a patient's tissue. It should also be appreciated that, while the figures illustrate one retractor 21 disposed on left support frame arm 11, one or more retractors 21 can also or alternatively be similarly disposed on right support frame 12.

In some embodiments, an underside of support body 13 can further include one or more hooks or posts 24 configured to receive and retain in position one or more additional retractors 25. For example, one or more additional retractors 25 can each be provided with a similar series of apertures 22b at a similar proximal end 23b of additional retractors 25, and such apertures 22b of additional retractors 25 are configured to receive one of hooks or posts 24 on underside of support body 13 and thereby retain proximal end(s) 23b of additional retractor(s) 25 on respective hooks or posts 24. As described above in connection with retractor(s) 21, retractors 25 may have any suitable shape. For example, retractors 25 may have at least one curved portion. For example, as illustrated in FIGS. 1, 3 and 4, proximal 23b and distal 26b ends of retractor 25 can be substantially curved. In some embodiments, retractors 25 may have at least one substantially straight portion. For example, as illustrated in FIGS. 1, 3 and 4, a medial portion of retractor 25 can be substantially straight. In some embodiments, at least a portion of retractor 25 can be tapered. For example, as illustrated in FIGS. 1, 3 and 4, in some embodiments, retractor 25 can taper along its length of extension at least from its medial portion to distal end 26b. Such a tapered aspect may allow retractors 25 to more effectively focus retention force to a particular portion of a patient's tissue.

In the manner described above, respective distal ends 26a, 26b of retractors 21, 25 may be adjustably positioned to retain and spread patient tissue at an incision made at a surgical access point on the patient. This allows the surgeon to securely place and hold a set of retractors 21, 25 during a surgical procedure without the need for additional surgical staff.

Figure 7:
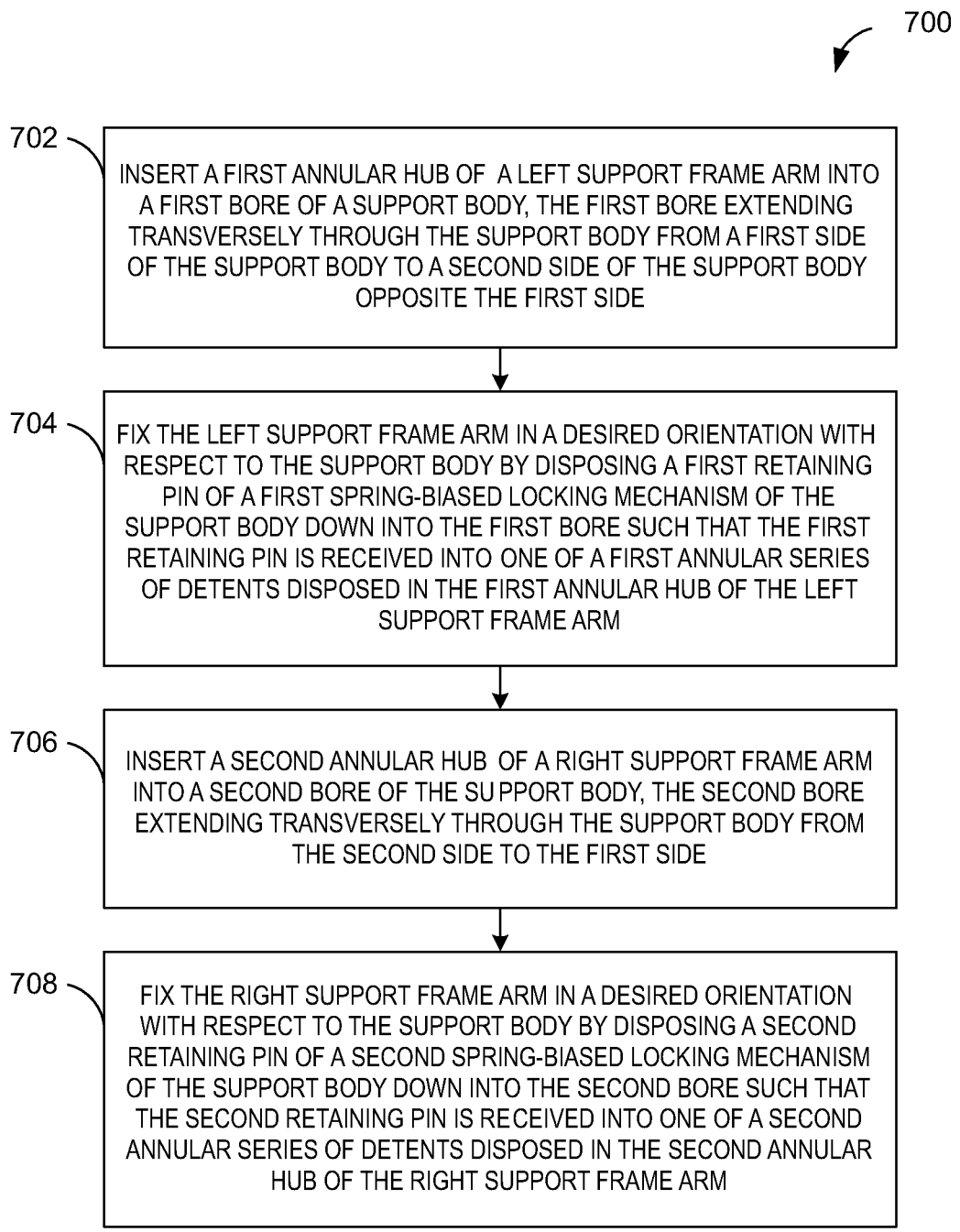
FIG. 7 illustrates a flowchart related to a method of using a retractor holding frame, in accordance with some embodiments.

Discussion now turns to an example method of using a retractor holding frame, for example, as that described in connection with any of FIGS. 1-6. FIG. 7 illustrates a flowchart 700 corresponding to such a method of use, in accordance with some embodiments. While flowchart 700 illustrates one or more actions and/or steps, it should be understood that one or more described actions can be omitted, one or more additional or alternative actions can be added, and/or one or more actions can be performed in another order than that specifically described without departing from the spirit or scope of the present disclosure.

Block 702 includes inserting a first annular hub of a left support frame arm into a first bore of a support body, the first bore extending transversely through the support body from a first side of the support body to a second side of the support body opposite the first side. For example, as previously described in connection with at least one figure, first annular hub 16a of left support frame arm 11 can be inserted into first bore 14 of support body 13. First bore 14 extends transversely through support body 13 from a first side of support body 13 to a second side of support body 13 opposite the first side.

In some embodiments, inserting the first annular hub of the left support frame arm into the first bore of the support body includes utilizing at least a portion of first spring-biased locking mechanism 18a to retract first retaining pin 17a sufficiently from first bore 14 to allow annular hub 16a of left support frame arm 11 to be inserted into first bore 14. In some embodiments, first annular hub 16a has a tapered distal end 27a configured to aid alignment between first annular hub 16a and first bore 14.

Block 704 includes fixing the left support frame arm in a desired orientation with respect to the support body by disposing a first retaining pin of a first spring-biased locking mechanism of the support body down into the first bore such that the first retaining pin is received into one of a first annular series of detents disposed in the first annular hub of the left support frame arm. For example, as previously described in connection with at least one figure, left support frame arm 11 can be fixed in a desired orientation with respect to support body 13 by disposing first retaining pin 17a of first spring-biased locking mechanism 18a of support body 13 down into first bore 14 such that first retaining pin 17a is received into one of a first annular series of detents 17a' disposed in annular hub 16a of left support frame arm 11.

In some embodiments, fixing the left support frame arm in the desired orientation with respect to the support body includes first rotating left support frame arm 11 to the desired orientation while its annular hub 16a is disposed within first bore 14 and first retaining pin 17a is retracted from first bore 14.

In some embodiments, left support frame arm 11 further comprises first plurality of posts 20a disposed along an outer edge of left support frame arm 11. In some such embodiments, flowchart 700 may further include securing one of a series of apertures 22a, disposed at a proximal end 23a of a first retractor 21, to one of the first plurality of posts 20a of left support frame arm 11 to thereby retain first retractor 21 in a first desired orientation.

Block 706 includes inserting a second annular hub of a right support frame arm into a second bore of the support body, the second bore extending transversely through the support body from the second side to the first side. For example, as previously described in connection with at least one figure, annular hub 16b of right support frame arm 12 can be inserted into second bore 15 of support body 13.

Second bore 15 extends transversely through support body 13 from the second side of support body 13 to the first side of support body 13.

In some embodiments, inserting the second annular hub of the right support frame arm into the second bore of the support body includes utilizing at least a portion of second spring-biased locking mechanism 18b to retract second retaining pin 17b sufficiently from second bore 15 to allow annular hub 16b of right support frame arm 12 to be inserted into second bore 15.

In some embodiments, second annular hub 16b has a tapered distal end 27b configured to aid alignment between second annular hub 16b and second bore 15.

Block 708 includes fixing the right support frame arm in a desired orientation with respect to the support body by disposing a second retaining pin of a second spring-biased locking mechanism of the support body down into the second bore such that the second retaining pin is received into one of a second annular series of detents disposed in the second annular hub of the right support frame arm. For example, as previously described in connection with at least one figure, right support frame arm 12 can be fixed in a desired orientation with respect to support body 13 by disposing second retaining pin 17a of second spring-biased locking mechanism 18b of support body 13 down into second bore 15 such that second retaining pin 17b is received into one of a second annular series of detents 17b' disposed in annular hub 16b of right support frame arm 12.

In some embodiments, fixing the right support frame arm in the desired orientation with respect to the support body includes first rotating right support frame arm 12 to the desired orientation while its annular hub 16b is disposed within second bore 15 and second retaining pin 17b is retracted from second bore 15.

In some embodiments, an underside of support body 13 further comprises at least one post 24 and flowchart 700 can further include securing one of a series of apertures 22b, disposed at a proximal end 23b of an additional retractor 25, to one of the at least one post 24 on the underside of support body 13 to thereby retain additional retractor 25 in an additional desired orientation.

In some embodiments, each of the first and second annular hubs 16a, 16b, first bore 14 and second bore 15 have a circular cross-section, thereby allowing the first annular hub 16ab to rotate within first bore 14 and left support frame arm 11 to rotate with respect to support body 13 and thereby allowing the second annular hub 16b to rotate within second bore 15 and right support frame arm 12 to rotate with respect to support body 13.

In some embodiments, support body 13 further includes quick-connect connector 28 and flowchart 700 can further include coupling support body 13 to a positioning arm utilizing quick-connect connector 28. In some embodiments, at least one respective portion of each of left and right support frame arms 11, 12 has a curved shape. In some embodiments, at least one respective portion of each of left and right support frame arms 11, 12 has a substantially straight shape. In some embodiments, at least one of first and second retractors 21 taper along their respective lengths. In some embodiments, first and second retractors 21 each comprise at least one curved portion.

Figure 8:
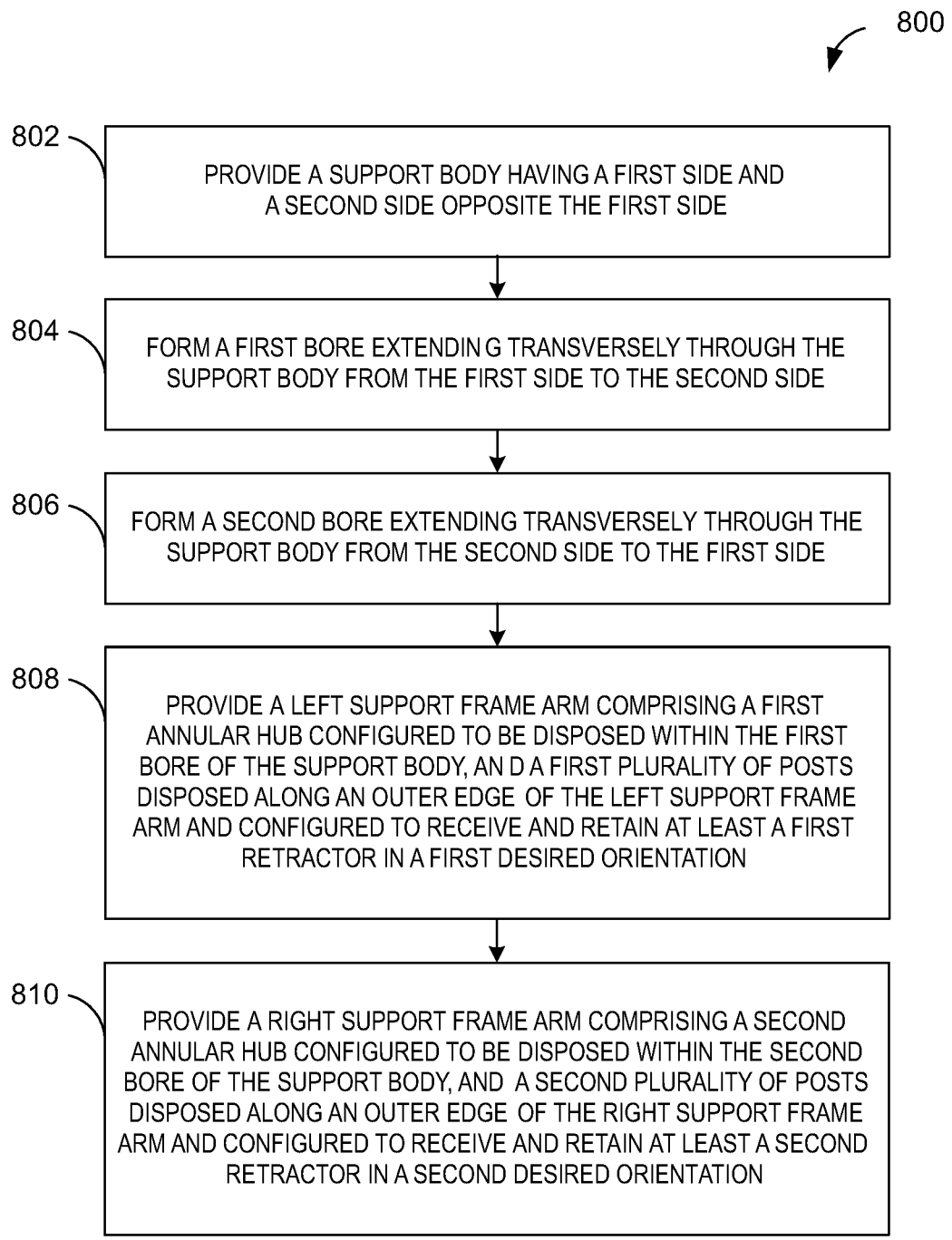
FIG. 8 illustrates a flowchart related to a method of manufacturing a retractor holding frame, in accordance with some embodiments.

Discussion now turns to an example method of manufacturing a retractor holding frame, for example, as that described in connection with any of FIGS. 1-7. FIG. 8 illustrates a flowchart 800 corresponding to such a method of manufacture, in accordance with some embodiments. While flowchart 800 illustrates one or more actions and/or steps, it should be understood that one or more described actions can be omitted, one or more additional or alternative actions can be added, and/or one or more actions can be performed in another order than that specifically described without departing from the spirit or scope of the present disclosure.

Block 802 includes providing a support body having a first side and a second side opposite the first side. For example, as previously described in connection with at least one figure, support body 13, having a first side and a second side opposite the first side, can be provided.

Block 804 includes forming a first bore extending transversely through the support body from the first side to the second side. For example, as previously described in connection with at least one figure, first bore 14 can be formed to extend transversely through support body 13 from a first side of support body 13 to a second side of support body 13 opposite the first side.

Block 806 includes forming a second bore extending transversely through the support body from the second side to the first side. For example, as previously described in connection with at least one figure, second bore 15 extends transversely through support body 13 from the second side of support body 13 to the first of support body 13.

Block 808 includes providing a left support frame arm comprising a first annular hub configured to be disposed within the first bore of the support body, and a first plurality of posts disposed along an outer edge of the left support frame arm and configured to receive and retain at least a first retractor in a first desired orientation. For example, as previously described in connection with at least one figure, left support frame arm 11 can be provided including annular hub 16a configured to be disposed within first bore 14 of support body 13, and a first plurality of posts 20a disposed along an outer edge of left support frame arm 11 and configured to receive and retain at least a first retractor 21 in a first desired orientation.

Block 810 includes providing a right support frame arm comprising a second annular hub configured to be disposed within the second bore of the support body, and a second plurality of posts disposed along an outer edge of the right support frame arm and configured to receive and retain at least a second retractor in a second desired orientation. For example, as previously described in connection with at least one figure, right support frame arm 12 can be provided including annular hub 16b configured to be disposed within second bore 15 of support body 13, and a second plurality of posts 20b disposed along an outer edge of right support frame arm 12 and configured to receive and retain at least a second retractor 21 in a second desired orientation.

In some embodiments, each of first and second annular hubs 16a, 16b, first bore 14 and second bore 15 are formed to have a circular cross-section, thereby allowing the first annular hub 16a to rotate within first bore 14 and left support frame arm 11 to rotate with respect to support body 13 and thereby allowing the second annular hub 16b to rotate within second bore 15 and right support frame arm 12 to rotate with respect to support body 13.

In some embodiments, flowchart 800 can further include disposing at least one post 24 on an underside of support body 13 such that the at least one post 24 is configured to receive and retain at least one additional retractor 25 in an additional desired orientation.

In some embodiments, flowchart 800 can further include forming a tapered distal end 27a on first annular hub 16a to aid alignment between first annular hub 16a and first bore 14. In some embodiments, flowchart 800 can further include forming a tapered distal end 27b on the second annular hub 16b to aid alignment between second annular hub 16b and second bore 15.

In some embodiments, flowchart 800 can further include providing a first spring-biased locking mechanism 18a, including a first retaining pin 17a configured to extend down into first bore 14, on support body 13. In some such embodiments, providing the first spring-biased locking mechanism includes providing at least a portion of the first spring-biased locking mechanism 18a that is configured to retract the first retaining pin 17a sufficiently from first bore 14 to allow first annular hub 16a to be inserted into first bore 14 or left support frame arm 11 to be rotated with respect to support body 13 while first annular hub 16a is disposed within first bore 14.

In some embodiments, flowchart 800 can further include providing second spring-biased locking mechanism 18b, including second retaining pin 17b configured to extend down into second bore 15, on support body 13. In some such embodiments, providing second spring-biased locking mechanism 18b includes providing at least a portion of second spring-biased locking mechanism 18b that is configured to retract second retaining pin 17b sufficiently from second bore 15 to allow second annular hub 16b to be inserted into second bore 15 or right support frame arm 12 to be rotated with respect to support body 13 while second annular hub 16b is disposed within second bore 15.

In some embodiments, flowchart 800 can further include forming a first annular series of detents 17a' in first annular hub 16a configured to selectively receive first retaining pin 17a and thereby fix left support frame arm 11 in a desired orientation with respect to support body 13. In some embodiments, flowchart 800 can further include forming a second annular series of detents 17b' in second annular hub 16b configured to selectively receive second retaining pin 17b and thereby fix right support frame arm 12 in a desired orientation with respect to support body 13.

In some embodiments, flowchart 800 can further include securing quick-connect connector 28 to support body 13, quick-connect connector 28 being configured to couple support body 13 to a positioning arm.

In some embodiments, at least one respective portion of each of left and right support frame arms 11, 12 has a curved shape. In some embodiments, at least one respective portion of each of left and right support frame arms 11, 12 has a substantially straight shape.

In some embodiments, flowchart 800 can further include providing the first retractor 21 having a series of apertures 22a disposed at proximal end 23b thereof, the series of apertures 22a configured to receive a post of first plurality of posts 20b of left support frame arm 11 and thereby retain proximal end 23a of first retractor 21 thereon.

In some embodiments, flowchart 800 can further include providing the second retractor 21 having a series of apertures 22a disposed at a proximal end 23a thereof, the series of apertures 22a configured to receive a post of the second plurality of posts 20b of right support frame arm 12 and thereby retain proximal end 23a of second retractor 21 thereon.

In some embodiments, flowchart 800 can further include providing the additional retractor 25 having a series of apertures 22b disposed at a proximal end 23b thereof, the series of apertures 22b configured to receive the at least one post 24 on the underside of support body 13 and thereby retain proximal end 23b of additional retractor 25 thereon.

In some embodiments, at least one of the first and second retractors 21 tapers along their respective lengths. In some embodiments, the first and second retractors 21 each comprise at least one curved portion.

Reference throughout this disclosure to "an embodiment" or "the embodiment" means that a particular feature, structure or characteristic described in connection with that embodiment is included in at least one embodiment. Thus, the quoted phrases, or variations thereof, as recited throughout this disclosure are not necessarily all referring to the same embodiment.

Similarly, it should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim in this or any application claiming priority to this application require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element.

While specific embodiments and applications of the present disclosure have been illustrated and described, it is to be understood that the disclosure is not limited to the precise configuration and components disclosed herein. Various modifications, changes, and variations which will be apparent to those skilled in the art may be made in the arrangement, operation, and details of the methods and systems of the present disclosure disclosed herein without departing from the spirit and scope of the disclosure.

What is claimed is:

1. A retractor holding frame, comprising:
    a support body comprising:
        a first bore extending transversely through the support body from a first side of the support body to a second side of the support body opposite the first side, and
        a second bore extending transversely through the support body from the second side to the first side;
    a left support frame arm comprising:
        a first annular hub configured to be disposed within the first bore of the support body, and
        a first plurality of posts disposed along an outer edge of the left support frame arm and configured to receive and retain at least a first retractor in a first orientation;
    a right support frame arm comprising:
        a second annular hub configured to be disposed within the second bore of the support body, and
        a second plurality of posts disposed along an outer edge of the right support frame arm and configured to receive and retain at least a second retractor in a second orientation; and
    the first retractor, wherein the first retractor comprises a first series of apertures disposed at a proximal end of the first retractor and configured to receive a post of the first plurality of posts of the left support frame arm and thereby retain the proximal end of the first retractor thereon,
    wherein each of the first annular hub, the second annular hub, the first bore and the second bore have a circular cross-section, thereby allowing the first annular hub to rotate within the first bore and the left support frame arm to rotate with respect to the support body and thereby allowing the second annular hub to rotate within the second bore and the right support frame arm to rotate with respect to the support body.

2. The retractor holding frame of claim 1, wherein:
the first annular hub has a tapered distal end configured to aid alignment between the first annular hub and the first bore; and
the second annular hub has a tapered distal end configured to aid alignment between the second annular hub and the second bore.

3. The retractor holding frame of claim 1, wherein:
the support body further comprises:
    a first spring-biased locking mechanism including a first retaining pin configured to extend down into the first bore, and
    a second spring-biased locking mechanism including a second retaining pin configured to extend down into the second bore;
the left support frame arm comprises a first annular series of detents configured to selectively receive the first retaining pin and thereby fix the left support frame in a desired orientation with respect to the support body; and
the right support frame arm comprises a second annular series of detents configured to selectively receive the second retaining pin and thereby fix the right support frame in a desired orientation with respect to the support body.

4. The retractor holding frame of claim 3, wherein:
at least a portion of the first spring-biased locking mechanism is configured to retract the first retaining pin at least partially from the first bore to allow the first annular hub to be inserted into the first bore or the left support frame arm to be rotated with respect to the support body while the first annular hub is disposed within the first bore; and
at least a portion of the second spring-biased locking mechanism is configured to retract the second retaining pin at least partially from the second bore to allow the second annular hub to be inserted into the second bore or the right support frame arm to be rotated with respect to the support body while the second annular hub is disposed within the second bore.

5. The retractor holding frame of claim 1, further comprising a second retractor, wherein the second retractor comprises a second series of apertures disposed at a proximal end of the second retractor and configured to receive a post of the second plurality of posts of the right support frame arm and thereby retain the proximal end of the second retractor thereon.

6. The retractor holding frame of claim 5, wherein at least one of the first and second retractors tapers along their respective lengths.

7. The retractor holding frame of claim 5, wherein the first and second retractors each comprise at least one curved portion.

8. A method of manufacturing a retractor holding frame, the method comprising:
providing a support body comprising a first side and a second side opposite the first side;
forming a first bore extending transversely through the support body from the first side to the second side;
forming a second bore extending transversely through the support body from the second side to the first side;
providing a left support frame arm comprising:
    a first annular hub configured to be disposed within the first bore of the support body, and
    a first plurality of posts disposed along an outer edge of the left support frame arm and configured to receive and retain at least a first retractor in a first orientation;
providing a right support frame arm comprising:
    a second annular hub configured to be disposed within the second bore of the support body, and
    a second plurality of posts disposed along an outer edge of the right support frame arm and configured to receive and retain at least a second retractor in a second orientation; and
providing the first retractor comprising a first series of apertures disposed at a proximal end of the first retractor and configured to receive a post of the first plurality of posts of the left support frame arm and thereby retain the proximal end of the first retractor thereon,
wherein each of the first annular hub, the second annular hub, the first bore and the second bore have a circular cross-section, thereby allowing the first annular hub to rotate within the first bore and the left support frame arm to rotate with respect to the suppor body and thereby allowing the second annular hub to rotate within the second bore and the right support frame arm to rotate with respect to the support body.

9. The method of claim 8, further comprising providing a second retractor comprising a second series of apertures disposed at a proximal end of the second retractor and configured to receive a post of the second plurality of posts of the right support frame arm and thereby retain the proximal end of the second retractor thereon.

10. The method of claim 9, wherein at least one of the first and second retractors tapers along their respective lengths.

11. The method of claim 10, wherein the first and second retractors each comprise at least one curved portion.

12. A retractor holding frame, comprising:
a support body comprising:
    a first bore extending transversely through the support body from a first side of the support body to a second side of the support body opposite the first side, and
    a second bore extending transversely through the support body from the second side to the first side;
a left support frame arm comprising:
    a first annular hub configured to be disposed within the first bore of the support body, and
    a first plurality of posts disposed along an outer edge of the left support frame arm and configured to receive and retain at least a first retractor in a first orientation;
a right support frame arm comprising:
    a second annular hub configured to be disposed within the second bore of the support body, and
    a second plurality of posts disposed along an outer edge of the right support frame arm and configured to receive and retain at least a second retractor in a second orientation; and
the first retractor, wherein the first retractor comprises a first series of apertures disposed at a proximal end of the first retractor and configured to receive a post of the first plurality of posts of the left support frame arm and thereby retain the proximal end of the first retractor thereon,
wherein an underside of the support body further comprises at least one post configured to receive and retain at least one additional retractor in a third orientation.

13. The retractor holding frame of claim 12, wherein:
the first annular hub has a tapered distal end configured to aid alignment between the first annular hub and the first bore; and
the second annular hub has a tapered distal end configured to aid alignment between the second annular hub and the second bore.

14. The retractor holding frame of claim 12, wherein:
the support body further comprises:
  a first spring-biased locking mechanism including a first retaining pin configured to extend down into the first bore, and
  a second spring-biased locking mechanism including a second retaining pin configured to extend down into the second bore;
the left support frame arm comprises a first annular series of detents configured to selectively receive the first retaining pin and thereby fix the left support frame in a desired orientation with respect to the support body; and
the right support frame arm comprises a second annular series of detents configured to selectively receive the second retaining pin and thereby fix the right support frame in a desired orientation with respect to the support body.

15. The retractor holding frame of claim 14, wherein:
at least a portion of the first spring-biased locking mechanism is configured to retract the first retaining pin at least partially from the first bore to allow the first annular hub to be inserted into the first bore or the left support frame arm to be rotated with respect to the support body while the first annular hub is disposed within the first bore; and
at least a portion of the second spring-biased locking mechanism is configured to retract the second retaining pin at least partially from the second bore to allow the second annular hub to be inserted into the second bore or the right support frame arm to be rotated with respect to the support body while the second annular hub is disposed within the second bore.

16. The retractor holding frame of claim 12, further comprising a second retractor, wherein the second retractor comprises a second series of apertures disposed at a proximal end of the second retractor and configured to receive a post of the second plurality of posts of the right support frame arm and thereby retain the proximal end of the second retractor thereon.

17. The retractor holding frame of claim 16, wherein at least one of the first and second retractors tapers along their respective lengths.

18. The retractor holding frame of claim 16, wherein the first and second retractors each comprise at least one curved portion.

* * * * *